(12) United States Patent
Koch

(10) Patent No.: US 7,354,451 B2
(45) Date of Patent: Apr. 8, 2008

(54) ACCOMMODATING INTRAOCULAR LENS IMPLANT

(76) Inventor: Paul S. Koch, 15 Red Oak Rd., East Greenwich, RI (US) 02818

( * ) Notice: Subject to any disclaimer, the term of this patent is extended or adjusted under 35 U.S.C. 154(b) by 0 days.

(21) Appl. No.: 11/119,655

(22) Filed: May 2, 2005

(65) Prior Publication Data

US 2006/0247767 A1 Nov. 2, 2006

(51) Int. Cl.
*A61F 2/16* (2006.01)
(52) U.S. Cl. .................. 623/6.37; 623/6.39; 623/6.43
(58) Field of Classification Search ............. 623/4.1, 623/6.11, 6.38–6.43, 6.45–6.47, 6.51–6.55
See application file for complete search history.

(56) References Cited

U.S. PATENT DOCUMENTS

| | | | |
|---|---|---|---|
| 4,446,581 A | 5/1984 | Blake | |
| 4,576,607 A | 3/1986 | Kelman | |
| 4,676,794 A | 6/1987 | Kelman | |
| 4,711,638 A * | 12/1987 | Lindstrom | ............ 623/6.54 |
| 4,863,465 A | 9/1989 | Kelman | |
| 4,871,363 A | 10/1989 | Kelman | |
| 5,133,749 A | 7/1992 | Nordan | |
| 5,197,981 A | 3/1993 | Southard | |
| 5,405,386 A | 4/1995 | Rheinish et al. | |
| 5,476,514 A | 12/1995 | Cumming | |
| 6,241,777 B1 | 6/2001 | Kellan | |
| 6,261,321 B1 | 7/2001 | Kellan | |
| 6,488,709 B1 | 12/2002 | Barrett | |
| 6,533,813 B1 | 3/2003 | Lin et al. | |
| 2001/0044657 A1 | 11/2001 | Kellan | |
| 2002/0095212 A1 | 7/2002 | Boehm | |
| 2002/0120331 A1 * | 8/2002 | Galin et al. | ............ 623/6.49 |
| 2003/0050695 A1 | 3/2003 | Lin et al. | |
| 2003/0130732 A1 | 7/2003 | Sarfarazi | |

OTHER PUBLICATIONS

U.S. Appl. No. 11/398,412, filed Apr. 5, 2006, Kellan, Robert E.

* cited by examiner

*Primary Examiner*—William H. Matthews
(74) *Attorney, Agent, or Firm*—Mark G. Lappin; Foley & Lardner LLP

(57) ABSTRACT

An accommodating intraocular lens implant for implantation in a human eye, including an optic adapted for coaxial alignment with a vision axis of the human eye, and at least one haptic. The haptic includes an anchor portion for receipt in one of a periphery of a capsular bag of the human eye, a ciliary sulcus of the human eye, and an angle of the anterior chamber of the human eye, and a sinuous portion extending radially from the optic and including a proximal end connected to the optic, a distal end spaced from the optic and connected to the anchor portion, and at least four curves successively connected between the proximal end and the distal end. The sinuous portion is adapted to flex upon ciliary muscle action to move the optic along the vision axis and allow the intraocular lens implant to automatically accommodate.

20 Claims, 4 Drawing Sheets

ACCOMMODATING INTRAOCULAR LENS IMPLANT

FIELD OF THE DISCLOSURE

The present disclosure relates to implantable intraocular lenses. Even more particularly, the present disclosure relates to a new and improved accommodating intraocular lens implant having an optic that can move forward and backward along a visual axis of an eye in response to vitreous pressure and contraction and relaxation of the ciliary muscle.

BACKGROUND OF THE DISCLOSURE

The crystalline lens is a transparent structure that focuses light in the human eye. Opacification of the lens known as cataract formation is a common cause of poor vision in the elderly, and can be corrected surgically.

Modern cataract surgery is performed by manual extracapsular cataract extraction, or by phacoemulsification. In both operations an opening is made in the anterior capsule to allow removal of the lens contents. The capsular bag remnant, however, is left in situ to provide support for an intraocular lens implant which is inserted following removal of the cataract to replace the focusing power of the natural crystalline lens.

It is known to provide an intraocular lens implant which typically comprises a central focusing element, known as an optic, and peripheral support structure, known as a haptic. The optic and the haptic of the intraocular lens may be manufactured from transparent rigid plastics material such as polymethyl methacrylate, or from flexible plastics material such as silicone or hydrogel. Intraocular lens implants manufactured from flexible material are preferable to those made of rigid material because the lens may be folded to allow insertion through a small incision in the sclera or outercoat of the eye and is then required to unfold to its original dimension.

The optic and haptic of the intraocular lens may be manufactured from the same material as a single piece unit or the haptic may be attached to the optic by a variety of mechanisms. There may be one or a plurality of haptics attached to the optic, although the most common configuration includes an optic with two outwardly extending haptics. The purpose of the haptic is to provide optimal centration of the optic as well as a means of fixation of the implant within a capsular bag remnant of the original lens following cataract or lens extraction. It is preferable that the haptics conform to the periphery of the capsular bag to provide a larger surface area of contact between the intraocular lens implant and the capsular bag and to ensure centration of the optic. It is also possible to implant a lens in front of the anterior capsule behind the iris with the haptics resting in the region between the root of the iris and ciliary processes, known as the cilairy sulcus. Intraocular lenses may also be inserted in phakic eyes to correct refractive errors, such as myopia or hyperopia, in front of the crystalline lens behind the iris with the haptic providing support in the cilairy sulcus. Furthermore, as an alternative site of implantation in phakic eyes, intraocular lenses may be inserted in front of the iris in the anterior chamber with the haptics resting in the angle of the anterior chamber.

A conventional intraocular lens 100 in accordance with the prior art shown in FIG. 1 comprises a central optic 101, and two haptics 102 connect with the central optic 101. As shown in FIG. 2, the conventional intraocular lens 100 is mounted in the capsular bag 200 of a human eye with the central optic 101 coaxially aligned with a vision axis A of the eye. However, an anterior chamber distance (ACD) is fixed (i.e., does not accommodate), the central optic 101 is not moveable along the vision axis A of the eye, and the refractive power of the lens cannot be adjusted. As shown in FIG. 3, the conventional intraocular lens 100 can also be mounted in the ciliary sulcus 300 of the human eye when the capsular bag 200 is not complete. The two haptics 102 of the conventional intraocular lens 100 are settled on the ciliary sulcus 300. However, the anterior chamber distance (ACD) is fixed, and the refractive power thereof cannot be adjusted.

Intraocular lenses differ with respect to their accommodation capability, and their placement in the eye. Accommodation is the ability of an intraocular lens to accommodate, which is to focus the eye for near and distant vision. Natural accommodation in a normal human eye involves shaping of the natural crystalline lens by automatic contraction and relaxation of the ciliary muscle of the eye by the brain to change the vitreous pressure of the eye and focus the eye at different distances. Ciliary muscle relaxation shapes the natural lens for distant vision. Ciliary muscle contraction shapes the natural lens for near vision.

Most non-accommodating implanted lenses have single focus optics which focus the eye at a certain fixed distance only and require the wearing of eye glasses to change the focus. Other non-accommodating lenses have bifocal optics which image both near and distant objects on the retina of the eye and provide both near vision and distant vision sight without eyeglasses. Bifocal intraocular lenses, however, suffer from the disadvantage that each bifocal image represents only about 40% of the available light and the remaining 20% of the light is lost in scatter.

What is still desired is a new and improved intraocular lens implant wherein the coaxial position of the central optic along the vision axis may be changed by control of the user and accommodate automatically. Preferably, the new and improved intraocular lens implant will utilize the ciliary muscle action and the vitreous pressure of the eye to effect accommodation movement of the lens optic along the vision axis of the eye between a distant vision position to a near vision position.

SUMMARY OF THE DISCLOSURE

In accordance with one aspect of the present disclosure there is provided a new and improved accommodating intraocular lens implant for implantation in a human eye. The lens implant includes an optic adapted for coaxial alignment with a vision axis of the human eye, and at least one haptic. The haptic includes an anchor portion for receipt in a periphery of a capsular bag of the human eye, a ciliary sulcus of the human eye, or an angle of the anterior chamber of the human eye. The haptic also includes a sinuous portion extending radially outwardly from a circumference of the optic and including a proximal end connected to the optic, a distal end spaced from the optic and connected to the anchor portion, and at least four curves successively connected between the proximal end and the distal end. The sinuous portion flexes upon ciliary muscle action to move the optic along the vision axis and allow the intraocular lens implant to automatically accommodate.

According to one aspect of the present disclosure, the sinuous portion also includes connecting segments extending in alternating directions and successively connecting the proximal end, the curves and the distal end of the sinuous portion.

Among other aspects and benefits, the new and improved intraocular lens implant of the present disclosure allows the coaxial position of the optic along the vision axis to be changed by control of the user such that the intraocular lens implant accommodates automatically. The new and improved intraocular lens implant utilizes the ciliary muscle action and the vitreous pressure of the eye to effect accommodation movement of the lens optic along the vision axis of the eye between a distant vision position to a near vision position. The new and improved intraocular lens implant is simple in design and can be folded for insertion into the eye.

Additional aspects and advantages of the present disclosure will become readily apparent to those skilled in this art from the following detailed description, wherein only an exemplary embodiment of the present disclosure is shown and described, simply by way of illustration of the best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

Reference is made to the attached drawings, wherein elements having the same reference character designations represent like elements throughout, and wherein.

DETAILED DESCRIPTION OF EXEMPLARY EMBODIMENT

Figure 1:
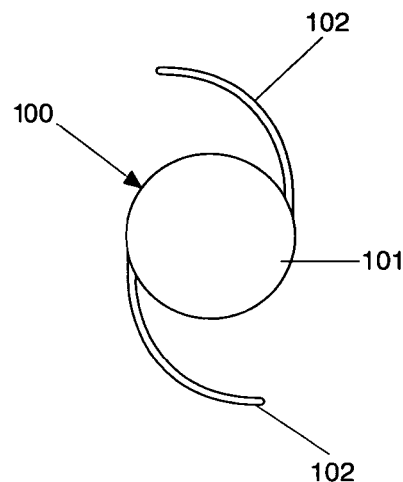
FIG. 1 is a front elevation view of a conventional intraocular lens in accordance with the prior art.
Figure 2:
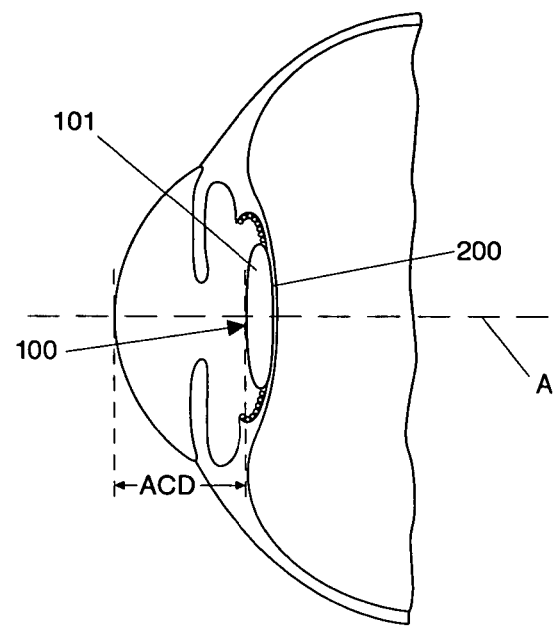
FIG. 2 is a side elevation view of the intraocular lens of FIG. 1 shown mounted in a capsular bag of a human eye and coaxially aligned with an imaginary vision axis of the eye.
Figure 3:
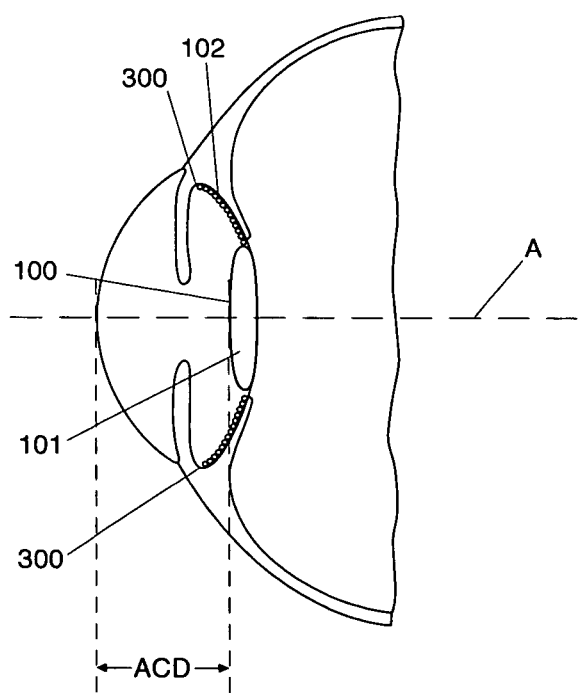
FIG. 3 is a side elevation view of the intraocular lens of FIG. 1 shown mounted in a ciliary sulcus of a human eye and coaxially aligned with an imaginary vision axis of the eye.
Figure 4:
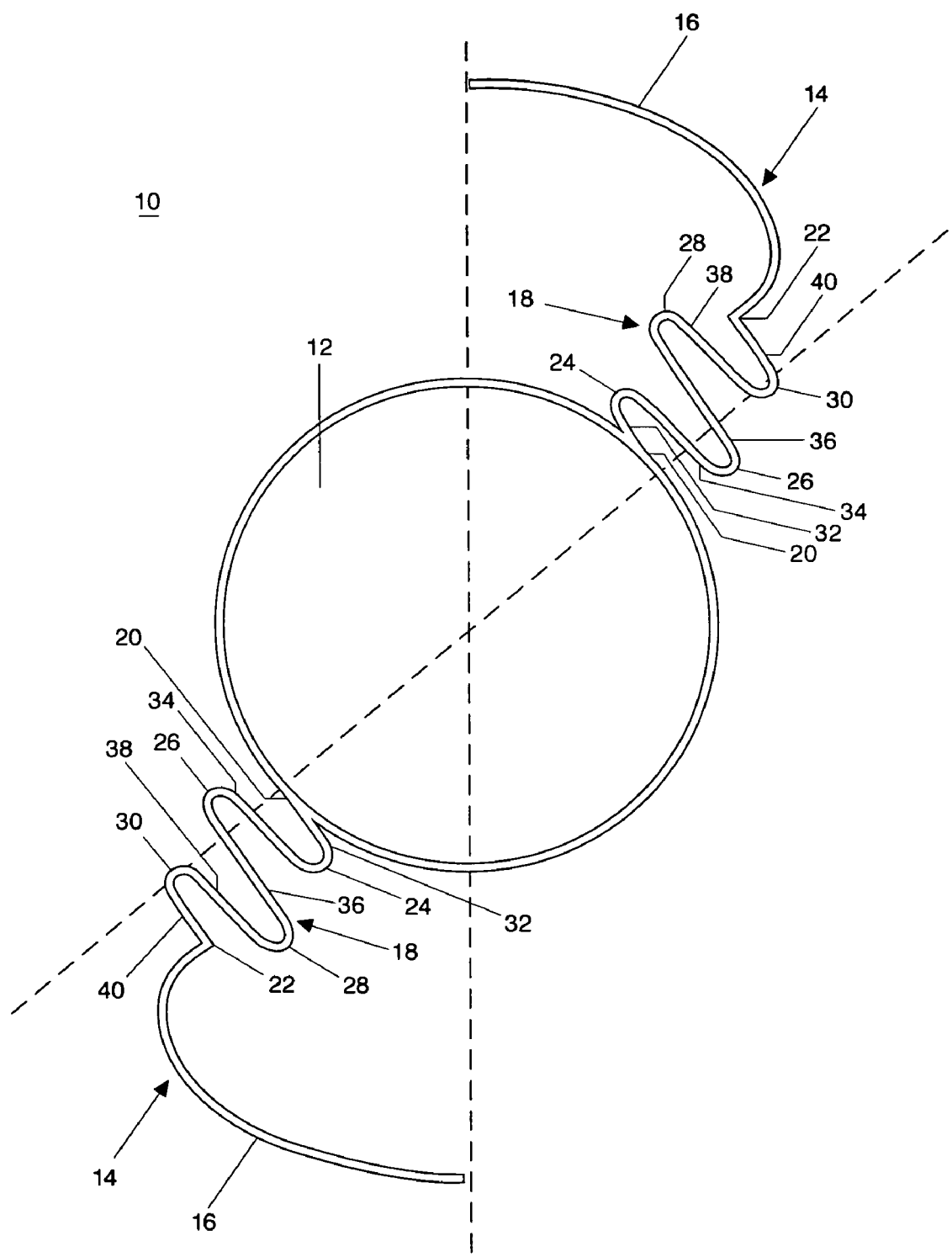
FIG. 4 is a front elevation view of an exemplary embodiment of an accommodating intraocular lens implant constructed in accordance with the present disclosure including an optic and a pair of haptics.
Figure 5:
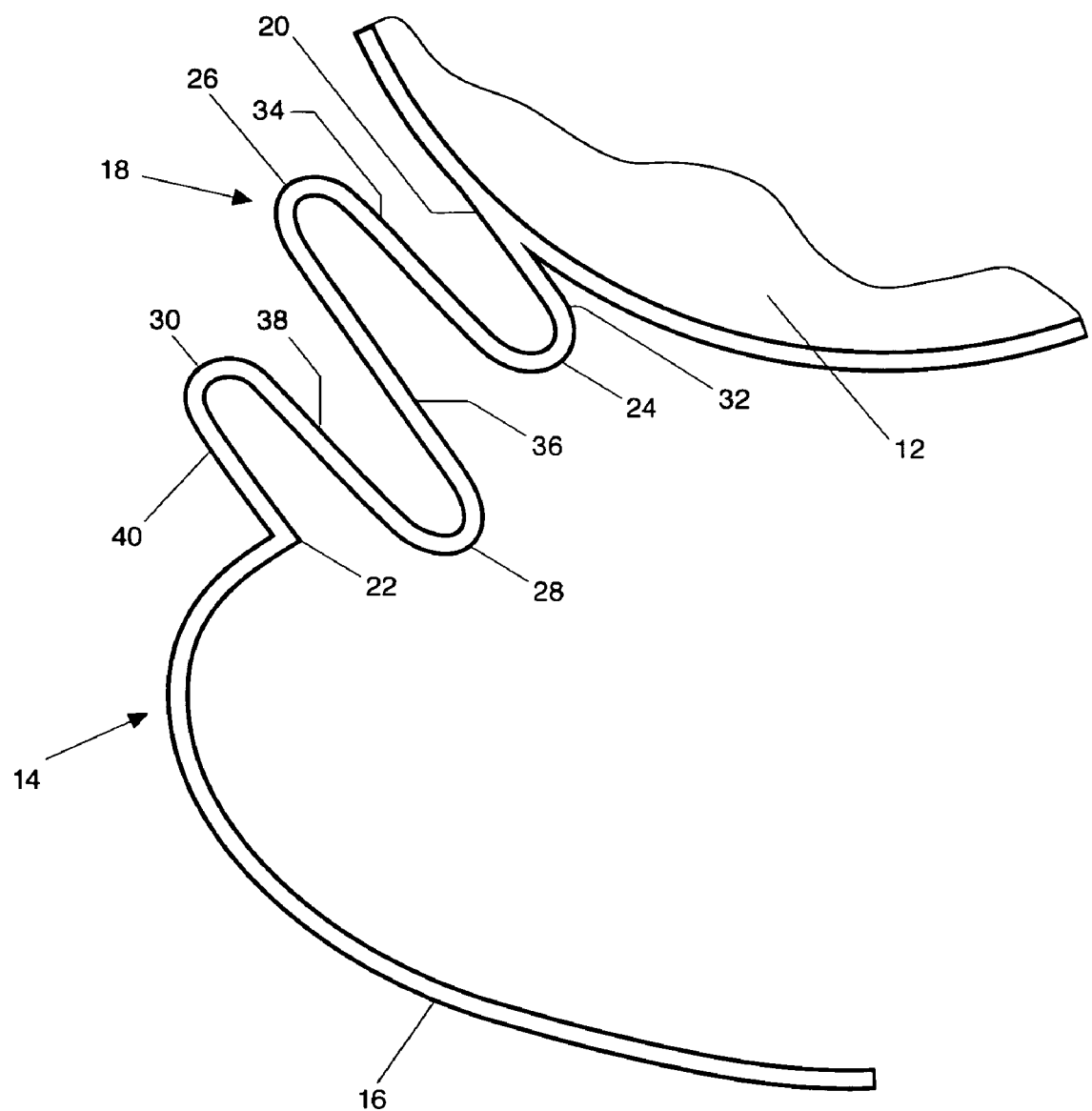
FIG. 5 is an enlarged front elevation view of one of the haptics of the intraocular lens implant of FIG. 4.
Figure 6:
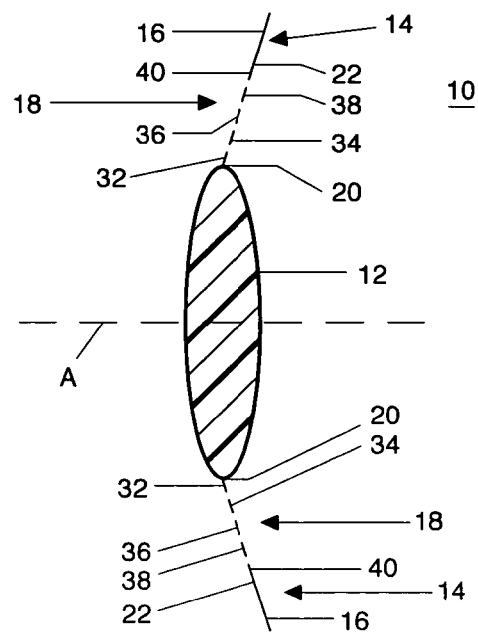
FIG. 6 is a sectional view of the intraocular lens implant of FIG. 4, wherein the optic is shown coaxially aligned with an imaginary vision axis of an eye.

In FIGS. 4-6 of the accompanying drawings, there is shown an exemplary embodiment of an accommodating intraocular lens implant 10 according to the present disclosure for implantation in a human eye. The accommodating intraocular lens implant 10 includes an optic 12 adapted for coaxial alignment with a vision axis A of the human eye, as shown in FIG. 6, and at least one haptic 14.

The haptic 14, which is shown best in FIG. 5, includes an anchor portion 16 for receipt in a periphery of a capsular bag of the human eye, a cilairy sulcus of the human eye, or an angle of the anterior chamber of the human eye, for example. The haptic 14 also includes a sinuous portion 18 extending radially outwardly from a circumference of the optic 12 and including a proximal end 20 connected to the optic 12, a distal end 22 spaced from the optic and connected to the anchor portion 16, and at least four curves 24, 26, 28, 30 successively connected between the proximal end 20 and the distal end 22. The sinuous portion 18 flexes upon ciliary muscle action and vitreous pressure to move the optic 12 along the vision axis A and allow the intraocular lens implant 10 to automatically accommodate.

In the exemplary embodiment shown, the sinuous portion 18 further includes five connecting segments 32, 34, 36, 38, 40 extending in alternating directions and successively connecting the proximal end 20, the curves 24, 26, 28, 30 and the distal end 22. As shown, the connecting segments 32, 34, 36, 38, 40 are generally straight but, in other embodiments, could be other than straight, such as curved, or even coiled.

In the exemplary embodiment shown, a first connecting segment 32 extends between the proximal end 20 of the sinuous portion 18 and a first curve 24, and the first connecting segment 32 extends tangentially from the circumference of the optic 12. A fifth connecting segment 40 extends between the distal end 22 of the sinuous portion 18 and a fourth curve 30, and the first and the fifth connecting segments 32, 40 have substantially equal lengths. A second connecting segment 34 of the sinuous portion 18 extends between the first curve 24 and a second curve 26, and a fourth connecting segment 38 extends between a third curve 28 and the fourth curve 30, and the second and fourth connecting segments 34, 38 have substantially equal lengths.

In the exemplary embodiment shown, the lengths of the second and the fourth connecting segments 34, 38 are greater than the lengths of the first and the fifth connecting segments 32, 40. A third, or middle, connecting segment 36 of the sinuous portion 18 extends between the second curve 26 and the third curve 28, and the third connecting segment 36 has a length greater then the lengths of the second and the fourth connecting segments 34, 38. The first, third and fifth connecting segments 32, 36, 40 of the sinuous portion 18 are parallel, and the second and fourth connecting segments 34, 38 are parallel.

As shown best in FIG. 6, the unflexed haptic 14 lies in a single plane. In the exemplary embodiment shown, the unflexed haptic 14 lies in a single plane extending from the optic 12 at an angle of about 5° to 30° to push the optic 12 firmly posterior against the capsular bag, so that vitreous pressure can compress the sinuous portions 18 and move the optic 12 forward. The sinuous portions 18, in one exemplary embodiment, will allow the optic 12 to move 1.0 mm, which in turn will provide 3.0 diopters of accommodation.

As shown in FIGS. 4 and 5, the anchor portion 16 of the haptic 14 extends radially outwardly from the sinuous portion 18 and then curves in an arcuate manner to a free distal end 42. In the exemplary embodiment shown, the anchor portion 16 curves in a counter-clockwise direction with respect to the optic 12. In alternative embodiments, the anchor portion 16 may curve in a clockwise direction with respect to the optic 12.

As shown best in FIGS. 4 and 6, the optic 12 is a substantially circular convex member, which may be manufactured from polymethyl methacrylate, or from flexible plastics material such as silicone or hydrogels. The haptics 14 may be manufactured from polymethyl methacrylate, or from flexible plastic materials such as silicone or hydrogels. In the exemplary embodiment shown, the intraocular lens implant 10 includes two of the haptics 14, and the proximal ends of the sinuous portions 18 of the haptics 14 are located at diametrically opposed locations of the optic 12. In alternative embodiments, the haptics 14 maybe located at locations other than diametrically opposed locations of the optic 12. In addition, the lens 10 implant may be provided with more than two of the haptics 14.

In the exemplary embodiment shown, the haptics 14 are integral formed with the optic 12 as a single piece. In alternative embodiments, the haptics 14 may be formed separately from the optic 12, and from material different from the optic 12, and then secured to the optic 12. According to one exemplary embodiment, the lens 10 implant, including the optic 12 and the haptics 14, is foldable for insertion into a small incision in a human eye during surgical implant.

The optic 12 can be provided with a diameter, for example, of between 4.5 mm and 7.0 mm, and the haptics 14 may be adapted to extend out to between 12.50 mm to 14.0 mm in order to fit both the capsular bag and the ciliary sulcus.

Figures 7, 8:
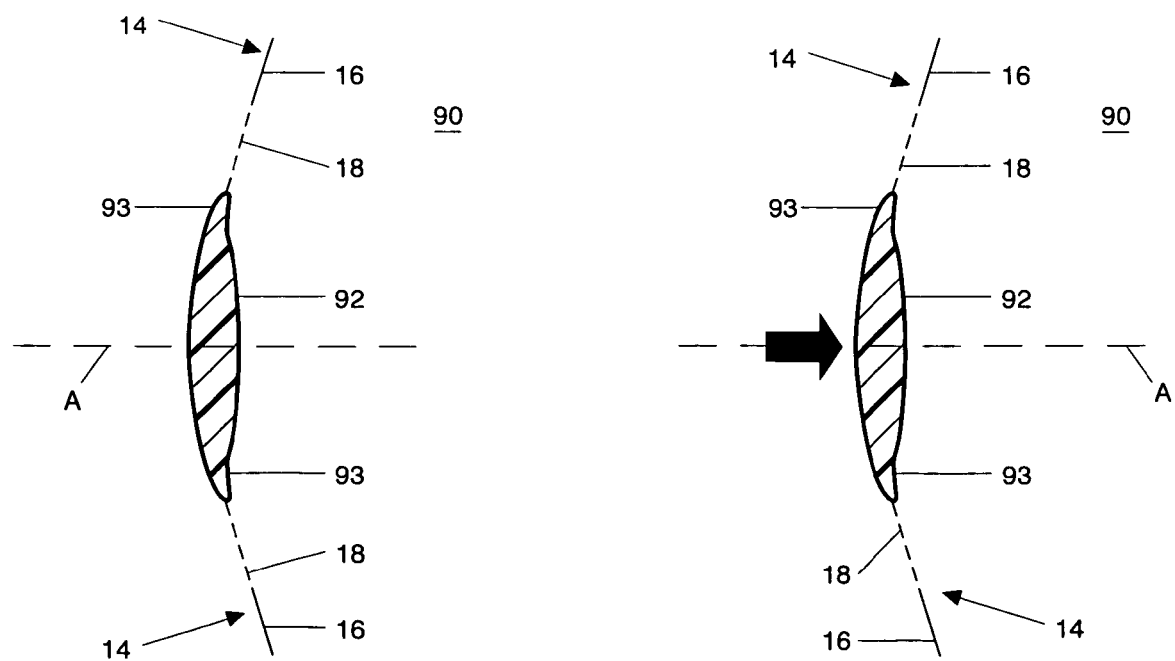
FIG. 7 is a sectional view of another exemplary embodiment of an accommodating intraocular lens implant constructed in accordance with the present disclosure, wherein an optic of the lens is shown coaxially aligned with an imaginary vision axis of an eye.
FIG. 8 is a sectional view of the intraocular lens implant of FIG. 7, wherein the optic is shown moving backwards along the imaginary vision axis of the eye while distal ends of haptics of the intraocular lens implant remain fixed and sinuous portions of the haptics flex in response, for example, to vitreous pressure and contraction of the ciliary muscle of the eye.

In FIGS. 7-8 of the accompanying drawings, there is shown another exemplary embodiment of an accommodating intraocular lens implant 90 according to the present disclosure for implantation in a human eye. The lens implant 90 is similar to the accommodating intraocular lens implant 10 of FIGS. 4-6, such that similar elements have the same reference numerals. The lens implant 90 of FIGS. 7-8, however, includes an optic 92 having radially extending ears 93, and the haptics 14 extend from the ears 93. The ears 93 extend in the same plane as the haptics 14 and enhance and stabilize the angulation of the haptics 14 by building the angulation into the periphery of the optic 92.

Numerous further modifications and alternative embodiments of the disclosure will be apparent to those skilled in the art in view of the foregoing description. This description is to be construed as illustrative only, and is for the purpose of teaching those skilled in the art the best mode of carrying out the disclosure. The details of the structure and method may be varied substantially without departing from the spirit of the disclosure, and the exclusive use of all modifications which come within the scope of the appended claims is reserved.

What is claimed is:

1. An accommodating intraocular lens implant for implantation in human eye, comprising:
    an optic adapted for coaxial alignment with vision axis for a human eye; and
    at least one flexible haptic including,
        an anchor portion for receipt in a periphery of a capsular bag of the human eye a ciliary sulcus of a human eye, or an angle of the anterior chamber of the human eye, and
        a sinuous portion extending radially outwardly from the circumference of the optic and including a proximal end connected to the optic and a distal end spaced from the optic and connected to the anchor portion, the sinuous portions including at least four curves successively connected between the proximal end and the distal end and disposed alternately on opposite sides, from one side to another, of an axis extending radially from said optic, wherein the sinuous portion is adapted to flex upon ciliary muscle action to move the optic along the vision axis and provide accommodation.

2. An accommodating intraocular lens implant according to claim 1, wherein the sinuous portion further includes five connecting segments extending in alternating directions and successively connecting the proximal end, the four curves and the distal end.

3. An accommodating intraocular lens implant according to claim 2, wherein a first connecting segment is straight and extends between the proximal end of the sinuous portion and a first curve, and the first connecting segment extends tangentially from a circumference of the optic.

4. An accommodating intraocular lens implant according to claim 2, wherein a first connecting segment of the sinuous portion extends between the proximal end of the sinuous portion and a first curve, and a fifth connecting segment extends between the distal end of the sinuous portion and a fourth curve, and the first and the fifth connecting segments have substantially equal lengths.

5. An accommodating intraocular lens implant according to claim 4, wherein a second connecting segment of the sinuous portion extends between the first curve and a second curve, and a fourth connecting segment extends between the fourth curve and a third curve, and the second and the fourth connecting segments have substantially equal lengths.

6. An accommodating intraocular lens implant according to claim 5, wherein the lengths of the second and the fourth connecting segments are greater than the lengths of the first and the fifth connecting segments.

7. An accommodating intraocular lens implant according to claim 6, wherein a third connecting segment of the sinuous portion extends between the second curve and the third curve, and the third connecting segment has a length greater then the lengths of the second and the fourth connecting segments.

8. An accommodating intraocular lens implant according to claim 7, wherein the connecting segments of the sinuous portion are straight and the first, third and fifth connecting segments are parallel, and the second and fourth connecting segments are parallel.

9. An accommodating intraocular lens implant according to claim 2, wherein lengths of the connecting segments of the sinuous portion vary.

10. An accommodating intraocular lens implant according to claim 2, wherein a central connecting segment of the sinuous portion is longest.

11. An accommodating intraocular lens implant according to claim 1, wherein the unflexed haptic lies in a single plane.

12. An accommodating intraocular lens implant according to claim 1, wherein the unflexed haptic lies in a single plane extending from the optic at an angle of about 5° to 30°.

13. An accommodating intraocular lens implant according to claim 1, wherein the optic includes a radially extending ear and the haptic extends from the ear.

14. An accommodating intraocular lens implant according to claim 1, wherein the anchor portion of the haptic extends outwardly from the sinuous portion in an arcuate manner.

15. An accommodating intraocular lens implant according to claim 14, wherein the anchor portion extends in a counter-clockwise direction with respect to the optic.

16. An accommodating intraocular lens implant according to claim 1, wherein the intraocular lens implant includes two of the haptics.

17. An intraocular lens implant according to claim 16, wherein the proximal ends of the sinuous portions of the haptics are located at diametrically opposed locations of the optic.

18. An intraocular lens implant according to claim 1, wherein the haptic is formed of a flexible plastics material.

19. An intraocular lens implant according to claim 1, wherein the haptic is integral with the optic.

20. An in intraocular lens implant according to claim 1, wherein the lens implant is foldable.

* * * * *

UNITED STATES PATENT AND TRADEMARK OFFICE
CERTIFICATE OF CORRECTION

PATENT NO. : 7,354,451 B2  Page 1 of 1
APPLICATION NO. : 11/119655
DATED : April 8, 2008
INVENTOR(S) : Paul S. Koch It is certified that error appears in the above-identified patent and that said Letters Patent is hereby corrected as shown below:

At Column 5, Line 56, Claim 1 currently reads as follows:
"capsular bag of the human eye a ciliary sulcus of a"

At Column 5, Line 56, please correct Claim 1 to read as follows:
-- capsular bag of the human eye, a ciliary sulcus of a --

Signed and Sealed this

Fifteenth Day of July, 2008

JON W. DUDAS
*Director of the United States Patent and Trademark Office*